United States Patent
Kono (10) Patent No.: US 10,451,597 B2
(45) Date of Patent: Oct. 22, 2019

(54) DETERMINATION DEVICE

(71) Applicant: DENSO CORPORATION, Kariya, Aichi-pref. (JP)

(72) Inventor: Yasushi Kono, Kariya (JP)

(73) Assignee: DENSO CORPORATION, Kariya (JP)

( * ) Notice: Subject to any disclaimer, the term of this patent is extended or adjusted under 35 U.S.C. 154(b) by 288 days.

(21) Appl. No.: 15/494,872

(22) Filed: Apr. 24, 2017

(65) Prior Publication Data

US 2017/0315104 A1    Nov. 2, 2017

(30) Foreign Application Priority Data

Apr. 29, 2016 (JP) .................................. 2016-92180
Jan. 25, 2017 (JP) .................................. 2017-11729

(51) Int. Cl.
*G01N 33/00* (2006.01)
*G01N 27/22* (2006.01)
*F02M 35/10* (2006.01)
*G01K 13/00* (2006.01)

(52) U.S. Cl.
CPC ..... *G01N 33/0006* (2013.01); *F02M 35/1038* (2013.01); *F02M 35/10393* (2013.01); *G01N 27/223* (2013.01); *G01K 13/00* (2013.01)

(58) Field of Classification Search
CPC ............. G01N 33/0006; G01N 27/223; F02M 35/10393; F01M 35/1038; G01K 13/00

USPC ..... 73/1.06, 335.01–335.05, 114.31, 114.37; 361/286; 702/104

See application file for complete search history.

(56) References Cited

U.S. PATENT DOCUMENTS

2014/0298880 A1*  10/2014  Pursifull ............ G01N 33/0006
                                                        73/1.06

FOREIGN PATENT DOCUMENTS

JP            2015-87196            5/2015

* cited by examiner

*Primary Examiner* — Robert R Raevis
(74) *Attorney, Agent, or Firm* — Nixon & Vanderhye, P.C.

(57) ABSTRACT

A determination device determining malfunction of a humidity sensor includes a malfunction determination portion. The humidity sensor includes a humidity detector, a temperature detector and a heater. The humidity detector has a humidity-sensitive film in an intake passage and detects a relative humidity of intake air taken into an internal combustion engine for a vehicle. The temperature detector detects a temperature of the humidity-sensitive film. The heater heats the humidity-sensitive film and the temperature of the humidity-sensitive film is increased by the heater. The malfunction determination portion estimates an estimated relative humidity at a subsequent temperature from an original relative humidity and the subsequent temperature, and compares the estimated relative humidity at the subsequent temperature and an actual subsequent relative humidity to determine malfunction of the humidity detector.

17 Claims, 11 Drawing Sheets

DETERMINATION DEVICE

CROSS REFERENCE TO RELATED APPLICATIONS

This application is based on Japanese Patent Applications No. 2016-92180 filed on Apr. 29, 2016 and No. 2017-11729 filed on Jan. 25, 2017, the disclosures of which are incorporated herein by reference.

TECHNICAL FIELD

The present disclosure relates to a determination device determining malfunction of a humidity sensor that measures a humidity of intake air taken into an internal combustion engine for a vehicle.

BACKGROUND

Recently, it has been required to measure a humidity of intake air in order to improve fuel consumption of an internal combustion engine and to clean exhaust gas.

The following humidity sensor has been known as one example of a humidity sensor measuring a humidity of intake air.

The humidity sensor includes a humidity detector, a temperature detector and a heater. The humidity detector has a humidity-sensitive film and detects a relative humidity of intake air based on a capacitance of the humidity-sensitive film. The intake air is taken into an internal combustion engine for a vehicle. The humidity-sensitive film is located in an intake passage where the intake air flows. The temperature detector detects a temperature of the humidity-sensitive film. The heater heats the humidity-sensitive film. The heater constantly heats the humidity-sensitive film to restrict dew condensation or fouling of the humidity-sensitive film. As such, humidity detection accuracy is maintained (for example, see JP 2015-87196 A).

For a factor of reducing the humidity detection accuracy, malfunction of the humidity detector itself is considered as well as the dew condensation or the fouling of the humidity-sensitive film.

However, in the humidity sensor disclosed in JP 2015-87196 A, the malfunction of the humidity sensor itself is not detected.

In the humidity sensor disclosed in JP 2015-87196 A, the heater continues to heat the humidity detector and the temperature detector. As a result, the temperature of the temperature detector is increased and detection accuracy of a temperature of the intake air is reduced. Also, the temperature of the humidity-sensitive film is increased as the temperature of the humidity detector is increased. As a result, detection accuracy of an absolute humidity is reduced. Furthermore, since the heater continues to heat, power consumption is also increased.

SUMMARY

It is an object of the present disclosure to provide a determination device capable of detecting malfunction of a humidity sensor that has a humidity-sensitive film located in an intake passage.

According to an aspect of the present disclosure, a determination device determines malfunction of a humidity sensor. The humidity sensor includes a humidity detector, a temperature detector and a heater. The humidity detector has a humidity-sensitive film and detects a relative humidity of intake air based on a capacitance of the humidity-sensitive film, the intake air being taken into an internal combustion engine for a vehicle, and the humidity-sensitive film being located in an intake passage where the intake air flows. The temperature detector detects a temperature of the humidity-sensitive film. The heater heats the humidity-sensitive film.

The temperature of the humidity-sensitive film is increased when the humidity-sensitive film is heated by the heater.

Hereinafter, the temperature detected at a predetermined time point is referred to as an original temperature. The relative humidity at the original temperature is referred to as an original relative humidity. The temperature detected after the heater starts heating or after the heater stops heating is referred to as a subsequent temperature, the subsequent temperature being different from the original temperature. The relative humidity at the subsequent temperature is referred to as a subsequent relative humidity.

The determination device includes a malfunction determination portion. The malfunction determination portion estimates an estimated relative humidity at the subsequent temperature from the original relative humidity and the subsequent temperature. The malfunction determination portion compares the estimated relative humidity at the subsequent temperature and the subsequent relative humidity to determine malfunction of the humidity detector.

According to the aspect of the present disclosure, the determination device compares the estimated relative humidity at the subsequent temperature and the actual subsequent relative humidity. For example, when a difference between the estimated relative humidity at the subsequent temperature and the actual subsequent relative humidity is quite larger than a predetermined difference, the determination device determines that the malfunction occurs in the humidity detector.

Accordingly, the determination device detects the malfunction of the humidity detector that has the humidity-sensitive film located in the intake passage.

The temperature outputted by the temperature detector includes an electrical signal that is converted into temperature, such as voltage.

Similarly, the relative humidity outputted by the humidity detector includes an electrical signal that is converted into relative humidity, such as voltage.

BRIEF DESCRIPTION OF THE DRAWINGS

The above and other objects, features and advantages of the present disclosure will become more apparent from the following detailed description made with reference to the accompanying drawings, in which like parts are designated by like reference numbers and in which.

DETAILED DESCRIPTION

Hereinafter, an embodiment of the present disclosure will be described. The following embodiment is just one example of the present disclosure and the present disclosure is not limited to the following embodiment.

[Structure]

An intake/exhaust system of an internal combustion engine 2 for a vehicle in which a humidity measurement device 1 is added will be described with reference to FIG. 1. The humidity measurement device 1 includes a humidity sensor 3 and a determination device 5, which will be described later.

The internal combustion engine 2 includes an intake passage 6 that leads intake air to cylinders and an exhaust passage 7 that discharges exhaust gas generated in the cylinders to the atmosphere.

The intake passage 6 includes internal passages such as an intake pipe, an intake manifold and intake ports.

The intake pipe is a passage member from an inlet of ambient air to the intake manifold. The intake pipe has an air cleaner 8, the humidity sensor 3, a flow rate sensor 9 and a throttle valve 10. The air cleaner 8 removes grid and dust included in the intake air. The humidity sensor 3 measures a humidity of the intake air. The flow rate sensor 9 measures a flow rate of the intake air. The throttle valve 10 adjusts the amount of the intake air supplied into the cylinders.

The intake passage 6 has an intake pressure sensor 11 that measures a pressure of the intake air at a downstream side of the throttle valve 10.

The intake manifold is a distribution pipe that distributes the intake air, which is supplied from the intake pipe, to cylinders of the internal combustion engine 2.

The intake ports are respectively provided to the cylinders at a cylinder head of the internal combustion engine 2. The intake ports lead the intake air, which is distributed by the intake manifold, to cylinders.

The exhaust passage 7 includes internal passages such as exhaust ports, an exhaust manifold and an exhaust pipe.

Similarly to the intake ports, the exhaust ports are respectively provided to the cylinders at the cylinder head of the internal combustion engine 2. The exhaust ports lead the exhaust gas, which is generated in the cylinders, to the exhaust manifold.

The exhaust manifold is a collecting pipe of the exhaust gas discharged from the exhaust ports.

The exhaust passage 7 has an air-fuel ratio sensor 12 that measures a concentration of oxygen in the exhaust gas.

The cylinder head, in which the intake ports and the exhaust ports are provided, includes intake valves and exhaust valves. Each of the intake valves opens and closes an exit end of the intake port of each cylinder. Each of the exhaust valves opens and closes an entrance end of the exhaust port of each cylinder.

An operation condition of the internal combustion engine 2 is controlled by an electronic control unit 13 (hereinafter, referred to as an ECU 13).

The ECU 13 receives signals from sensors that detect parameters indicating operation conditions or control conditions of the internal combustion engine 2. The ECU 13 includes an input circuit, a CPU, memories and an output circuit. The input circuit processes the inputted signals. The CPU executes a control processing or a calculation processing for controlling the internal combustion engine 2, according to the inputted signals. The memories store data, programs and the like for controlling the internal combustion engine 2. The output circuit outputs signals for controlling the internal combustion engine 2 according to processing results of the CPU.

The sensors outputting signals to the ECU 13 include an oil temperature sensor 14 and a rotation number sensor 15, other than the humidity sensor 3, the flow rate sensor 9, the intake pressure sensor 11 and the air-fuel ratio sensor 12. The oil temperature sensor 14 detects a temperature of operating oil of the internal combustion engine 2. The rotation number sensor 15 detects a rotation number of the internal combustion engine 2.

According to signals outputted from the above sensors, the ECU 13 controls the operation condition of the internal combustion engine 2 by controlling the throttle valve 10 to vary the flow rate of the intake air, and the ECU 13 controls a fuel injection valve 16 that injects fuel to vary a fuel injection amount to the internal combustion engine 2.

The ECU 13 includes the determination device 5, which will be described later.

Figure 2A:
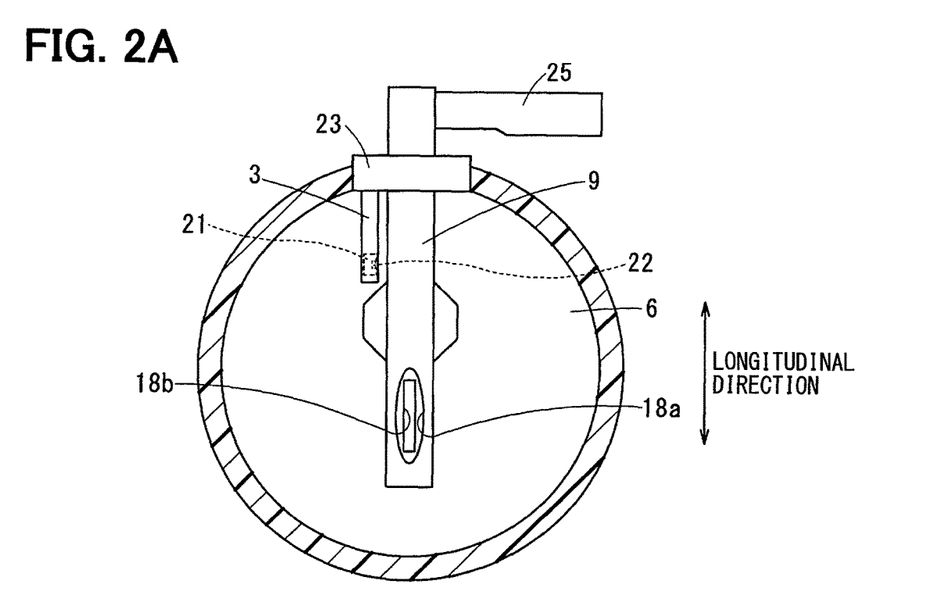
FIG. 2A is a cross-sectional view of a humidity sensor and a flow rate sensor viewed from an upstream side of intake air.
Figure 2B:
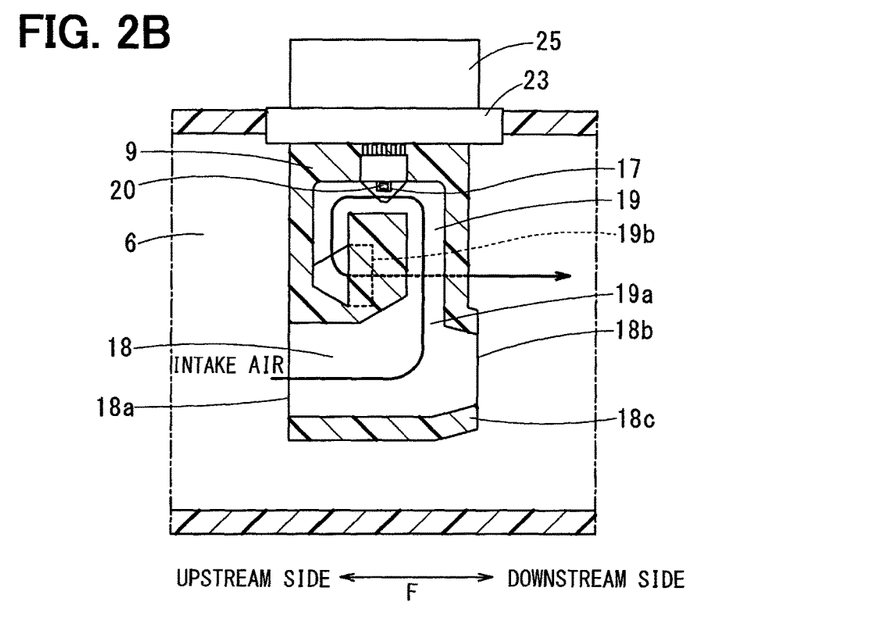
FIG. 2B is a cross-sectional view of the flow rate sensor along a flow direction of the intake air.

Details of the humidity sensor 3 and the flow rate sensor 9 of the present embodiment will be described with reference to FIG. 2A and FIG. 2B.

The flow rate sensor 9 is located in the intake passage 6.

Hereinafter, a direction along which the intake air flows in the intake passage 6 will be referred to as a direction F.

The flow rate sensor 9 has a flow rate sensor chip 17. The flow rate sensor 9 projects toward an inner periphery of the intake passage 6 and detects the flow rate of the intake air.

The flow rate sensor 9 is made of resin material. The flow rate sensor 9 has a lane inside of the flow rate sensor 9.

For example, the lane inside of the flow rate sensor 9 includes a bypass lane 18 and a sub-bypass lane 19.

A part of the intake air flowing in the intake passage 6 flows in the bypass lane 18. The bypass lane 18 extends along the direction F. The bypass lane 18 has an inlet 18a at an upstream side of the bypass lane 18, and has an outlet 18b at a downstream side of the bypass lane 18.

The bypass lane 18 has an outlet nozzle 18c at the downstream side of the bypass lane 18. The outlet nozzle 18c narrows the flow of the intake air passing through the bypass lane 18.

The sub-bypass lane 19 has an entrance 19a and an exit 19b. A part of the intake air flowing in the bypass lane 18 and narrowed by the outlet nozzle 18c flows into the entrance 19a. The exit 19b returns the intake air passing through the sub-bypass lane 19 to the intake passage 6. The intake air flowing from the entrance 19a turns around in the flow rate sensor 9 and flows toward the exit 19b.

The flow rate sensor chip 17 has a flow rate detector that outputs the flow rate. The flow rate detector has a flow rate detection element 20 that is sensitive to the flow rate of the intake air. The flow rate detection element 20 is a heat transfer type element that measures the flow rate according to heat transfer of the intake air flowing in the sub-bypass lane 19. The flow rate detection element 20 has a well-known structure having a heat resistor and a temperature measurement resistor on a surface.

The flow rate outputted from the flow rate detector includes an electrical signal that is converted into the flow rate, such as a voltage.

The humidity sensor 3 has a humidity sensor chip 21 and detects the humidity of the intake air. The humidity sensor 3 projects toward the inner periphery of the intake passage 6. The humidity sensor 3 is apart from the flow rate sensor 9.

When a direction along which the humidity sensor 3 projects is referred to as a longitudinal direction, the humidity sensor 3 projects such that the longitudinal direction is orthogonal to the direction F.

For example, the humidity sensor chip 21 has a humidity-sensitive film 22 that is sensitive to the humidity of the intake air. The humidity sensor chip 21 has the humidity-sensitive film 22 on the surface of the humidity sensor chip 21. The humidity sensor chip 21 is disposed on the humidity sensor 3 such that the humidity-sensitive film 22 is exposed to the intake passage 6. Specifically, the humidity sensor chip 21 is disposed on the humidity sensor 3 such that a surface of the humidity-sensitive film 22 is parallel to the longitudinal direction and the direction F.

For example, the humidity sensor chip 21 is a capacitance type in which a capacitance of the humidity-sensitive film 22 varies according to humidity, and the humidity sensor chip 21 outputs a relative humidity. The humidity-sensitive film 22 is a polymer film. The amount of water molecule taken into the humidity-sensitive film 22 varies according to humidity of surrounding atmosphere. As a result, the capacitance of the humidity-sensitive film 22 varies according to the humidity.

Figure 3:
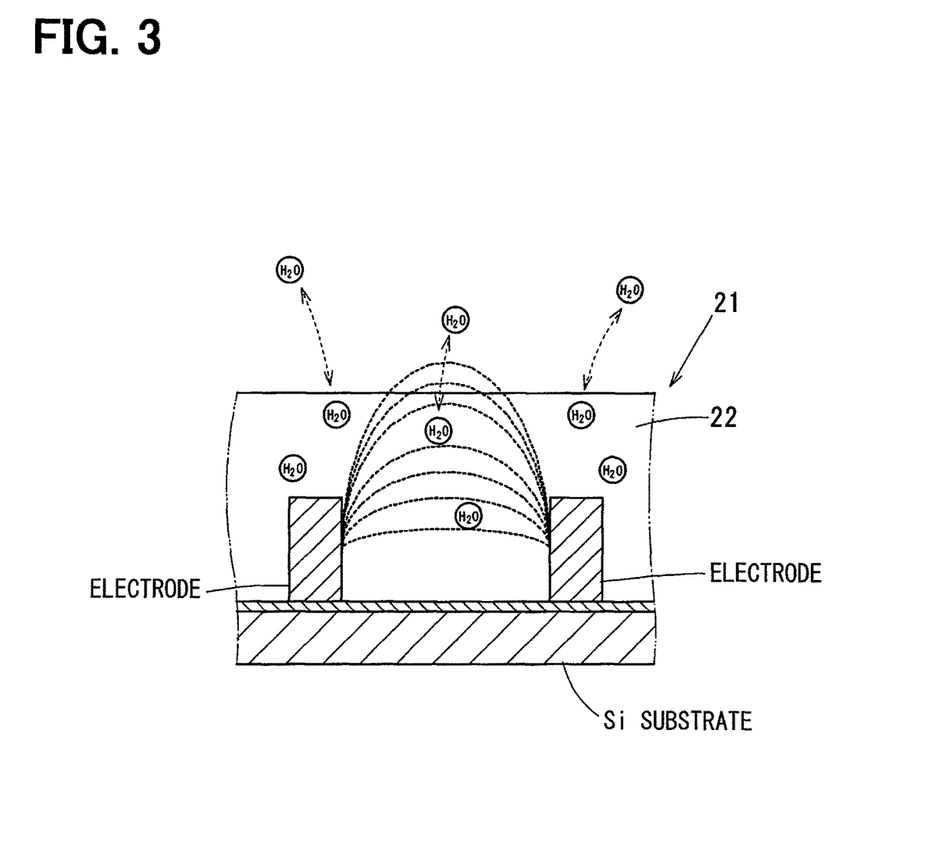
FIG. 3 is an explanatory diagram of a humidity-sensitive film.

Specifically, as shown in FIG. 3, the humidity sensor chip 21 has a structure in which an amount of the water molecule according to the humidity of the surrounding atmosphere is taken into the humidity-sensitive film 22 and a capacitance detected between electrodes varies. In FIG. 3, broken lines express lines of electrical force.

The humidity sensor 3 and the flow rate sensor 9 are connected to a base 23. That is, the base 23 is a root from which the humidity sensor 3 and the flow rate sensor 9 project. The base 23 is formed by accommodating ends of the humidity sensor 3 and the flow rate sensor 9 in a metal mold and injecting melted resin in the metal mold.

The intake passage 6 has an equipment hole penetrating the intake passage 6 from outside to inside at a position at which the humidity sensor 3 and the flow rate sensor 9 are equipped. The base 23 is embedded in the equipment hole to be fixed to the intake passage 6. As such, the humidity sensor 3 and the flow rate sensor 9 are fixed to the intake passage 6.

A connector 25 is attached to the base 23 and a terminal of the connector 25 outputs signals of the flow rate and the relative humidity. The flow rate and the relative humidity are outputted from the same terminal.

Figure 4:
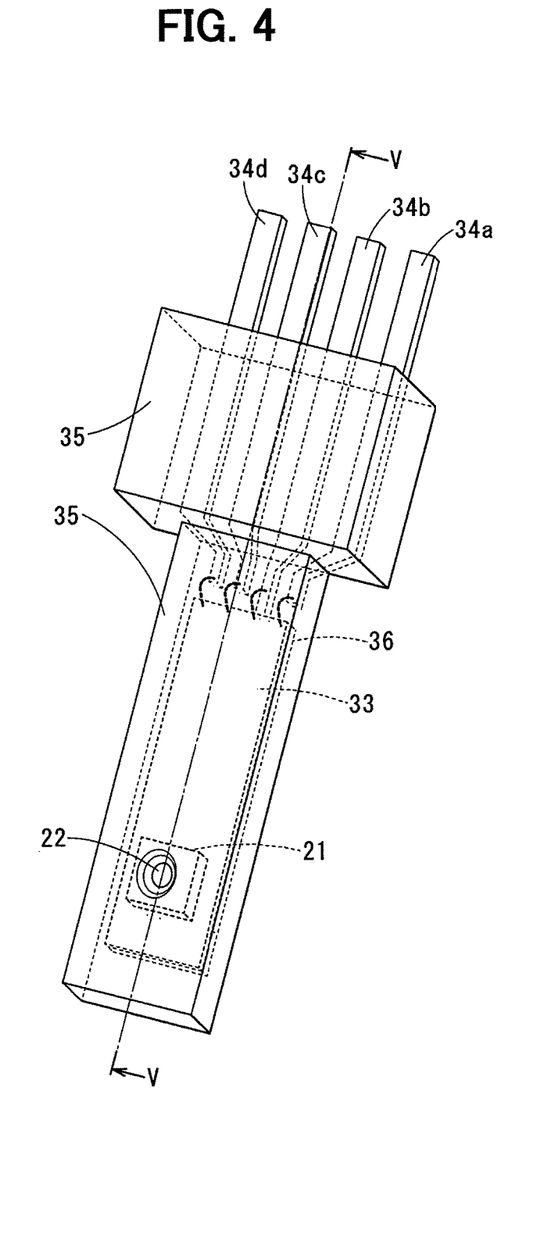
FIG. 4 is a perspective view of the humidity sensor.

As shown in FIG. 4, the humidity sensor 3 includes the humidity sensor chip 21, a circuit board 33 and lead frames 34a to 34d. The humidity sensor chip 21 is mounted on the circuit board 33 and the circuit board 33 is made of FPC. The lead frames 34a to 34d are connected to terminals of the circuit board 33 by wire-bonding. The entire portion of the humidity sensor 3 is molded by a resin member 35.

The lead frame 34b includes a mount portion 36 and the circuit board 33 is mounted on an end portion of the mount portion 36. End portions of the lead frames 34a to 34d opposite to the mount portion 36, a surface of the mount portion 36 on which the circuit board 33 is not mounted, and the humidity-sensitive film 22 of the humidity sensor chip 21 are exposed from the resin member 35.

A part of the mount portion 36 is exposed from the resin member toward the intake passage 6 and the part of the mount portion 36 is exposed to the intake air. As a result, a temperature of the humidity sensor chip 21 is almost the same as the temperature of the intake air.

The end portions of the lead frames 34a to 34d opposite to the mount portion 36 are electrically connected to the terminal of the connector 25. The lead frames 34a to 34d, except for the mount portion 36, are implanted in the base 23.

The lead frame 34a is connected to a direct current voltage source, and the lead frame 34b is connected to the ground. The lead frames 34c and 34d interchange data signals with the ECU 13 according to, for example, I2C protocol.

Figure 5:
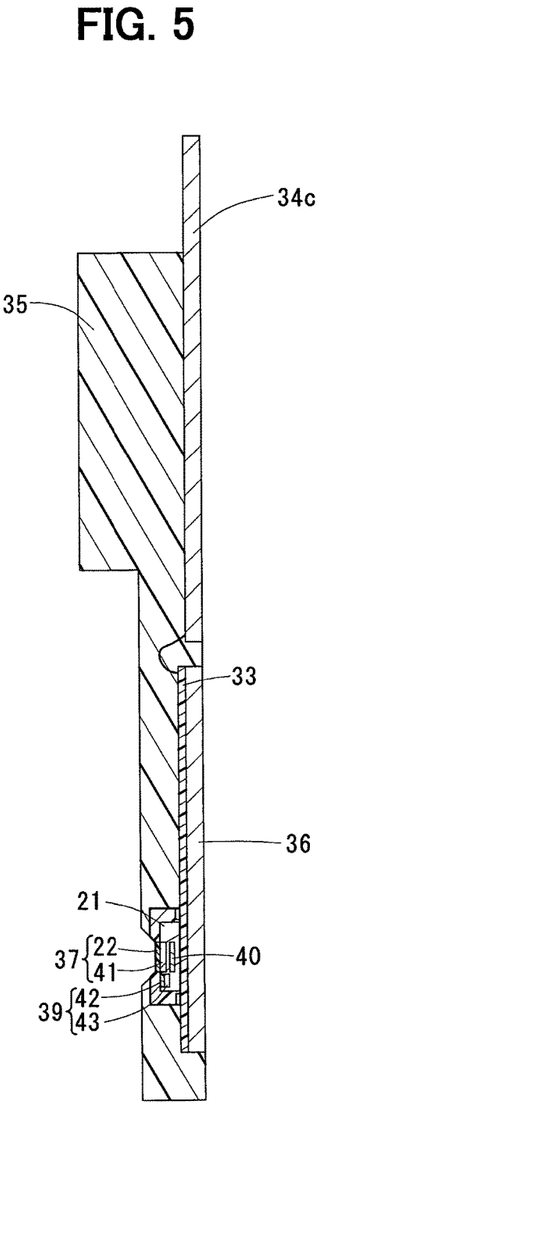
FIG. 5 is a cross-sectional view of the humidity sensor taken along a line V-V of FIG. 4.

As shown in FIG. 5, the humidity sensor chip 21 includes a humidity detector 37, a temperature detector 39 and a heater 40.

The humidity detector 37 includes the humidity-sensitive film 22 and a relative humidity output portion 41. The relative humidity output portion 41 detects the relative humidity from the capacitance of the humidity-sensitive film 22 and outputs a voltage signal corresponding to the relative humidity.

The temperature detector 39 includes a temperature measurement portion 42 and a temperature output portion 43. The temperature measurement portion 42 detects a temperature of the humidity-sensitive film 22. The temperature output portion 43 detects a temperature from a signal of the temperature measurement portion 42 and outputs a voltage signal corresponding to the temperature.

The hart portion 40 is disposed close to the humidity-sensitive film 22 and heats the humidity-sensitive film 22.

The humidity sensor chip 21 is activated by the voltage of the DC voltage source provided through the lead frames 34a and 34b. The humidity sensor chip 21 outputs signals such as the relative humidity and heats the humidity-sensitive film 22 by the heater 40 according to commend signals of the ECU 13 provided through the lead frames 34c and 34d.

Next, characteristic structure of the present embodiment will be described.

The humidity measurement device 1 of the present embodiment has the determination device 5.

Figure 1:
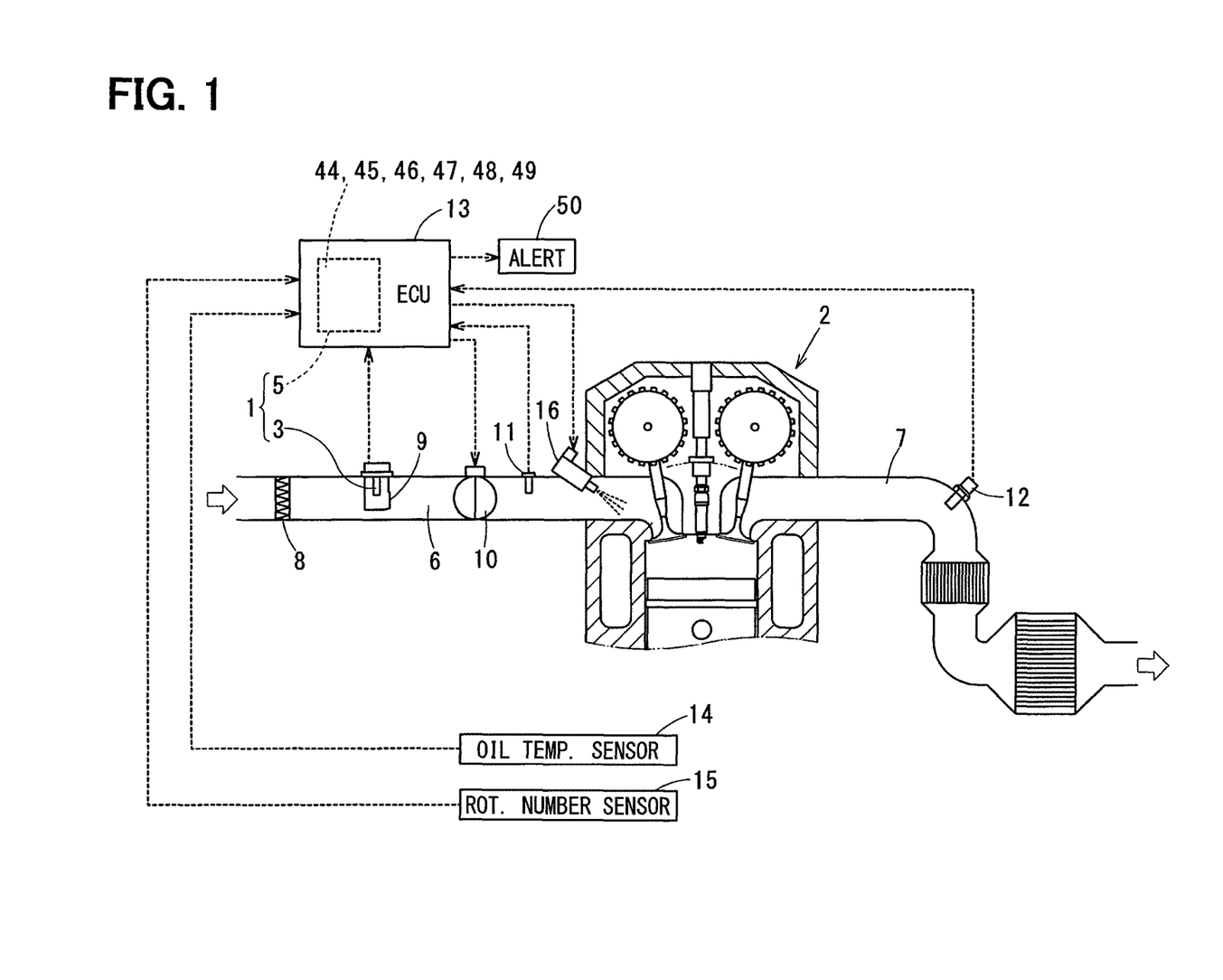
FIG. 1 is a diagram illustrating an intake/exhaust system of an internal combustion engine for a vehicle.

The determination device 5 includes a heat command portion 44 and a malfunction determination portion 45 (see FIG. 1). The heat command portion 44 allows the heater 40 to increase the temperature of the humidity-sensitive film 22, that is, to heat the humidity-sensitive film 22. The malfunction determination portion 45 determines malfunction of the humidity detector 37 by comparing an estimated relative humidity at a subsequent temperature and a subsequent relative humidity. The estimated relative humidity at the subsequent temperature is estimated from an original relative humidity and the subsequent temperature.

The original temperature is defined as a temperature detected before the temperature of the humidity-sensitive film 22 is increased by the heater 40. The original relative humidity is defined as a relative humidity at the original temperature. The subsequent temperature is defined as a temperature detected after the temperature of the humidity-sensitive film 22 is increased by the heater 40. The subsequent relative humidity is defined as a relative humidity at the subsequent temperature.

Figure 11A:
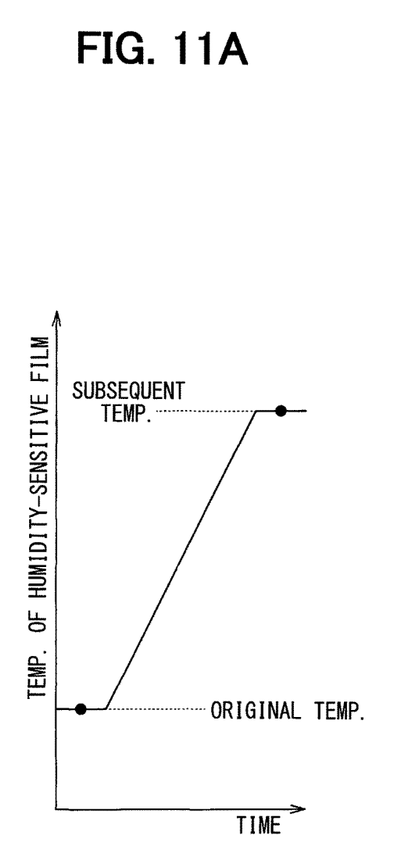
FIGS. 11A and 11B are explanatory diagrams of an original temperature and a subsequent temperature according to an embodiment.

As shown in FIG. 11A, the original temperature and the subsequent temperature may be temperatures in a constant temperature state before or after the temperature increase. Alternatively, as shown in FIG. 11B, the original temperature and the subsequent temperature may be temperatures during the temperature increase.

Figure 11B:
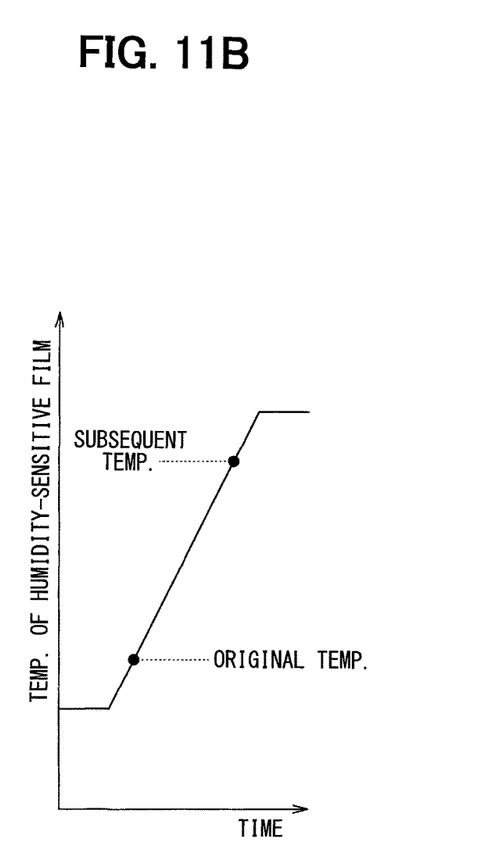

In FIG. 11A and FIG. 11B, each black spot expresses a detection time point of the original temperature and the subsequent temperature.

The malfunction determination portion 45 determines the malfunction of the humidity detector 37 when other device does not execute any control based on the relative humidity.

The control of the other device is executed based on the relative humidity after the malfunction determination portion 45 determines the malfunction and the temperature becomes equal to the original temperature.

The determination device 5 further includes an abnormality determination portion 46, a humidity determination portion 47, a condition determination portion 48 and a cumulated number determination portion 49 (see FIG. 1).

The abnormality determination portion 46 determines whether a detected relative humidity of the humidity detector 37 is abnormal by comparing the estimated relative humidity at the subsequent temperature and the subsequent relative humidity.

The humidity determination portion 47 determines whether both original relative humidity and subsequent relative humidity are equal to or higher than 90 percent when the abnormality determination portion 46 determines that the detected relative humidity is abnormal.

The condition determination portion 48 determines whether a predetermined condition is satisfied when the humidity determination portion 47 determines that both original relative humidity and subsequent relative humidity are equal to or more than 90 percent.

The predetermined condition is defined as a condition where the temperature of the intake air is equal to or higher than 30 degrees Celsius and the temperature of the operating oil of the internal combustion engine 2 is equal to or higher than 80 degrees Celsius.

The cumulated number determination portion 49 increases the cumulated number by one when the condition determination portion 48 determines that the predetermined condition is satisfied and the cumulated number determination portion 49 determines whether the cumulated number is more than 5.

The malfunction determination portion 45 does not determine the malfunction when the temperature of the intake air is equal to or lower than 10 degrees Celsius.

When the determination device 5 determines that the malfunction occurs in the humidity detector 37, the determination device 5 outputs a signal to activate an alert portion 50 (see FIG. 1).

[Control Processing]

Figure 6:
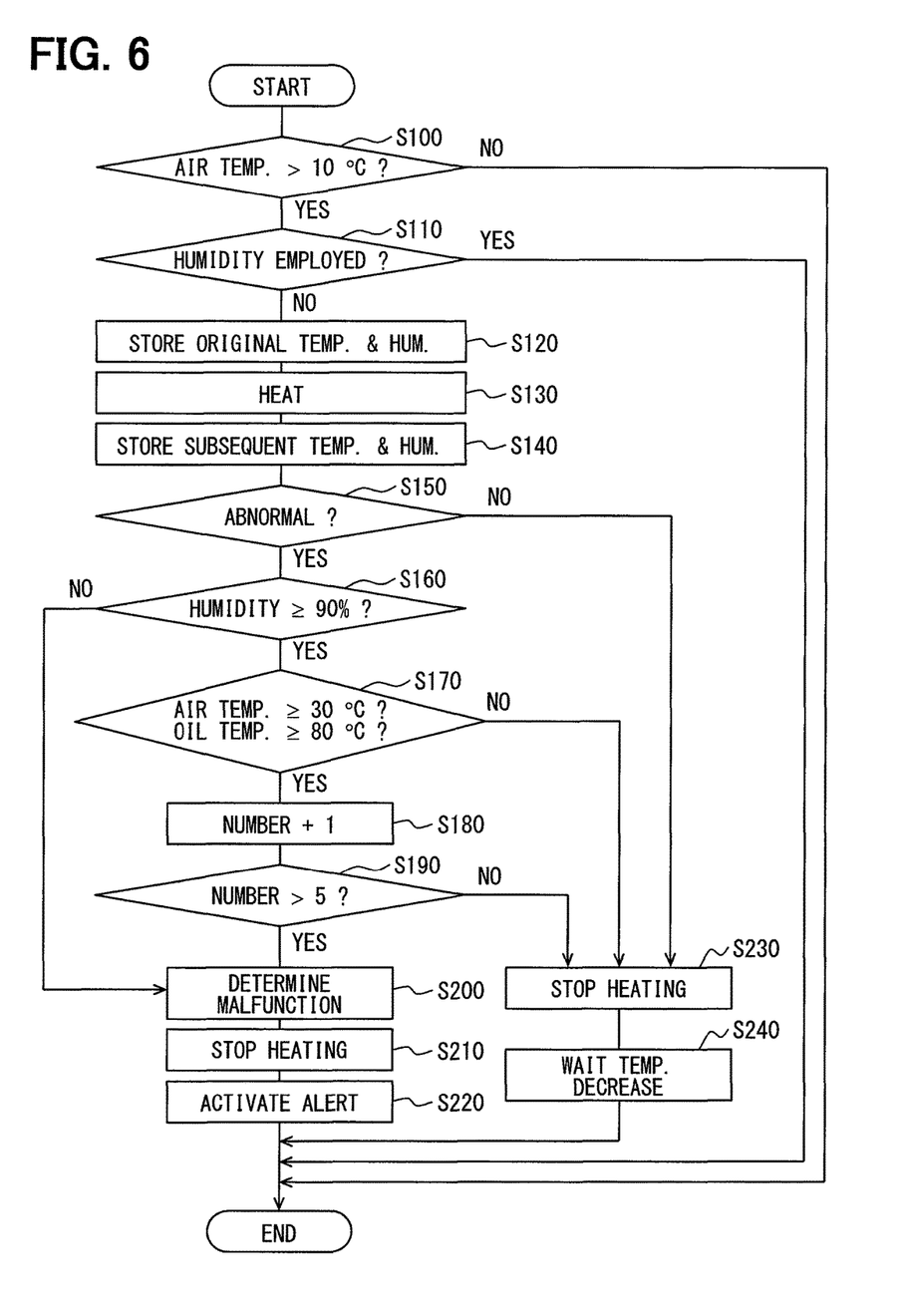
FIG. 6 is a flowchart illustrating a control processing of a determination device.

An example of the control processing of the determination device 5 of the present embodiment will be described with reference to FIG. 6.

First, at S100, the determination device 5 determines whether the temperature of the intake air is higher than 10 degrees Celsius.

When the temperature of the intake air is higher than 10 degrees Celsius (i.e., YES), the processing proceeds to S110.

When the temperature of the intake air is equal to or lower than 10 degrees Celsius (i.e., NO), the determination device 5 finishes the processing.

In this case, the temperature of the intake air corresponds to the temperature outputted by the temperature detector 39.

Next, at S110, the determination device 5 determines whether the relative humidity is employed in the control of the other device. In this case, the other device is, for example, the throttle valve 10 or the fuel injection valve 16.

When the determination device 5 determines that the relative humidity is employed in the control of the other device (i.e., YES), the determination device 5 finishes the processing.

When the determination device 5 determines that the relative humidity is not employed in the control of the other device, the processing proceeds to S120.

A situation when the relative humidity is not employed in the control of the other device is, for example, a situation when energization of the humidity detector 37 is started, a situation when a speed of the vehicle is reduced, or a situation when the vehicle is stopped.

The situation when the energization of the humidity detector 37 is started is before the control of the internal combustion engine 2 employing the relative humidity is started. That is, when the energization of the humidity detector 37 is started, the relative humidity is not employed in the control of the other device. When the speed of the vehicle is reduced, fuel supply to the internal combustion engine 2 is suspended. In this case, the control of the internal combustion engine 2 employing the relative humidity is not executed, and thus the relative humidity is not employed in the control of the other device. When the vehicle is stopped, the relative humidity is not employed in the control of the other device.

Next, at S120, the humidity sensor chip 21 outputs the relative humidity and the temperature to the ECU 13 as the determination device 5, and the ECU 13 stores the relative humidity and the temperature in the memory or the like as the original relative humidity and the original temperature. Then, the processing proceeds to S130.

Next, at S130, the temperature of the humidity-sensitive film 22 is increased by the heater 40.

A situation where the temperature of the humidity-sensitive film 22 is increased by the heater 40 includes a situation where a condition of the humidity-sensitive film 22 is shifted from a condition not heated by the heater 40 to a condition heated by the heater 40, and also includes a situation where the condition of the humidity-sensitive film 22 is shifted from a condition heated by the heater 40 to a condition further heated by the heater 40.

The processing at S130 corresponds to a function of the heat command portion 44.

Then the processing proceeds to S140.

Next, at S140, the humidity sensor chip 21 outputs the relative humidity and the temperature to the ECU 13 as the determination device 5, and the ECU 13 stores the relative humidity and the temperature in the memory or the like as the subsequent relative humidity and the subsequent temperature. Then, the processing proceeds to S150.

Next, at S150, the determination device 5 determines whether the detected relative humidity is abnormal by comparing the estimated relative humidity at the subsequent temperature, which is estimated from the original relative humidity and the subsequent temperature, and the subsequent relative humidity.

The processing at S150 corresponds to a function of the abnormality determination portion 46.

Figure 7:
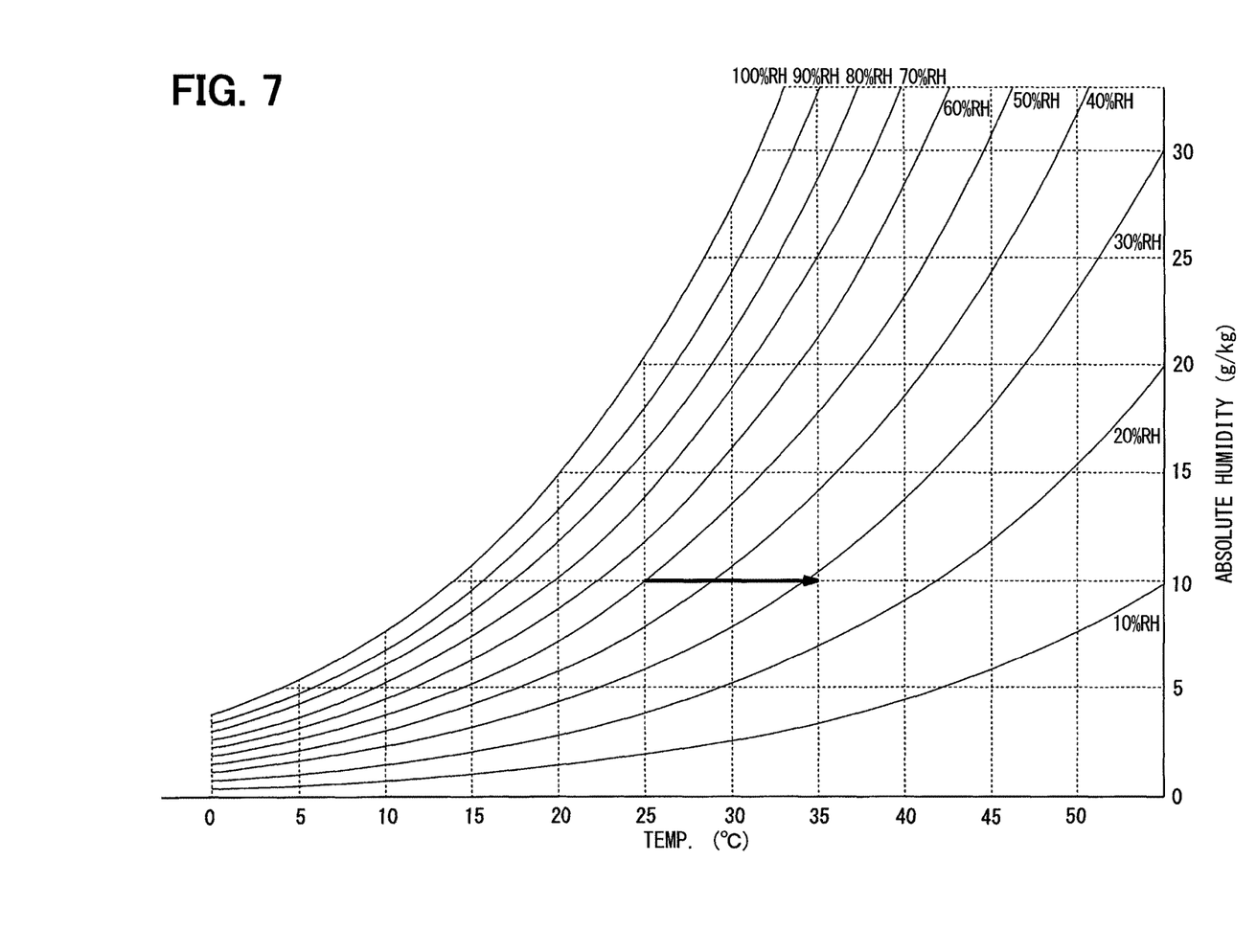
FIG. 7 is an explanatory diagram of a procedure to evaluate an estimated relative humidity at a subsequent temperature with a psychrometric chart.

More specifically, by employing a psychrometric chart shown in FIG. 7, the absolute humidity is calculated from the original relative humidity. For example, when the original temperature is 25 degrees Celsius and the original relative humidity is 50 percent, the absolute humidity is 10 g/Kg. Even when the humidity-sensitive film 22 is heated, the absolute humidity does not vary. Therefore, the relative humidity at the subsequent temperature is estimated from the psychrometric chart. For example, when the subsequent temperature is 35 degrees Celsius and the absolute humidity is 10 g/Kg, the estimated relative humidity is 28.3 percent. The determination device 5 determines whether the detected relative humidity of the humidity detector 37 is abnormal, based on whether the estimated relative humidity at the subsequent temperature is substantially equal to the subsequent relative humidity (see FIGS. 8A and 8B). An arrow shown in FIG. 7 expresses a variation of the relative humidity corresponding to a temperature variation of FIG. 8A.

The psychrometric chart is preliminary stored in the memory or the like of the ECU 13 as a data set or a calculating formula.

At S150, when the determination device 5 determines that the detected relative humidity is abnormal (i.e., YES; see broken lines of FIG. 8B), the processing proceeds to S160.

When the determination device 5 determines that the detected relative humidity is not abnormal (i.e., NO), the processing proceeds to S230 and the heating of the humidity-sensitive film 22 by the heater 40 is suspended. Then, the processing proceeds to S240. The determination device 5 waits until the temperature of the humidity-sensitive film 22, detected by the temperature detector 39, becomes equal to the original temperature, and the determination device 5 finishes the processing.

After the processing is finished, the control of the other device is executed based on the relative humidity.

Figure 8A:
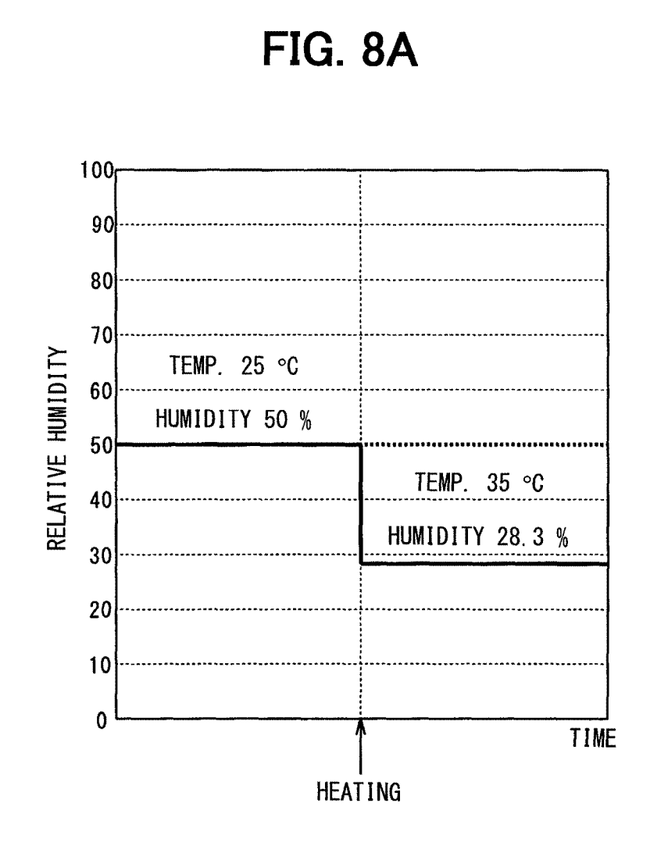
FIG. 8A is an explanatory diagram of variation of the relative humidity before or after a heating, in a normal state.
Figure 8B:
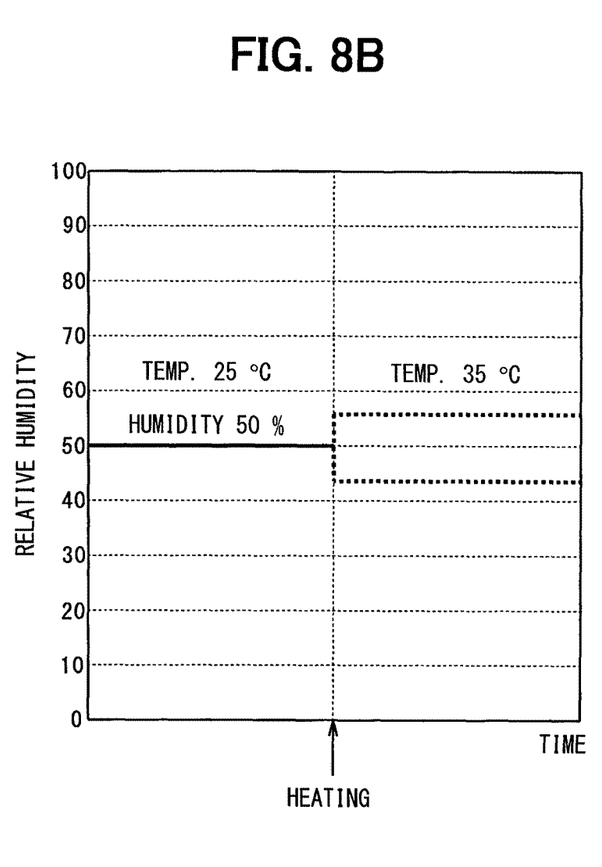
FIG. 8B is an explanatory diagram of variation of the relative humidity before or after the heating, in an abnormal state.

Each of FIG. 8A and FIG. 8B expresses time variations of the original temperature, original relative humidity, subsequent temperature and subsequent humidity before or after the humidity-sensitive film 22 is heated.

Next, at S160, the determination device 5 determines whether the original relative humidity and the subsequent relative humidity are equal to or higher than 90 percent.

When the determination device 5 determines that the original relative humidity and the subsequent relative humidity are equal to or higher than 90 percent (i.e., YES; see FIG. 9B), the processing proceeds to S170.

When the determination device 5 determines that the subsequent relative humidity is lower than 90 percent (i.e., NO; see FIG. 9A), the processing proceeds to S200.

The processing at S160 corresponds to a function of the humidity determination portion 47.

Figure 9A:
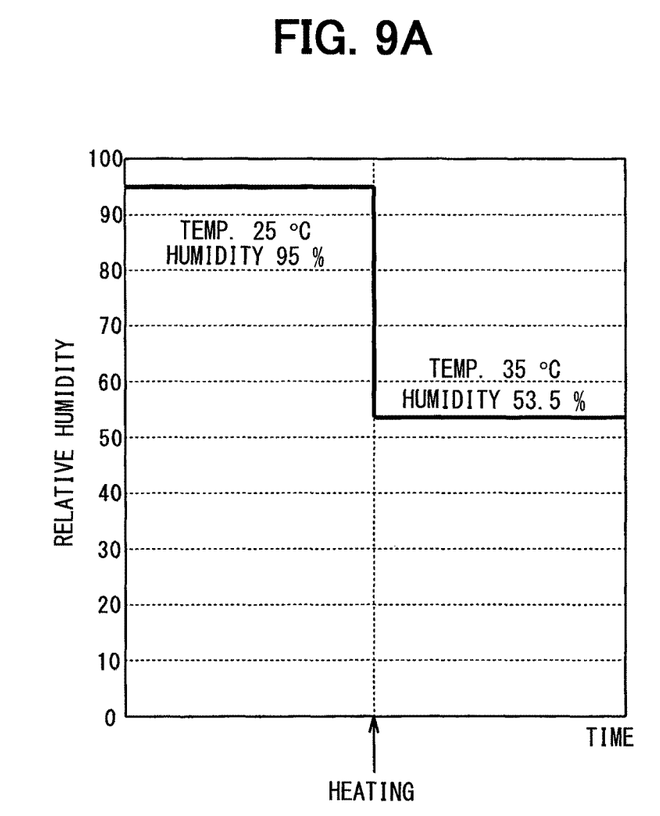
FIG. 9A is an explanatory diagram of variation of the relative humidity before or after a heating, in a normal state.
Figure 9B:
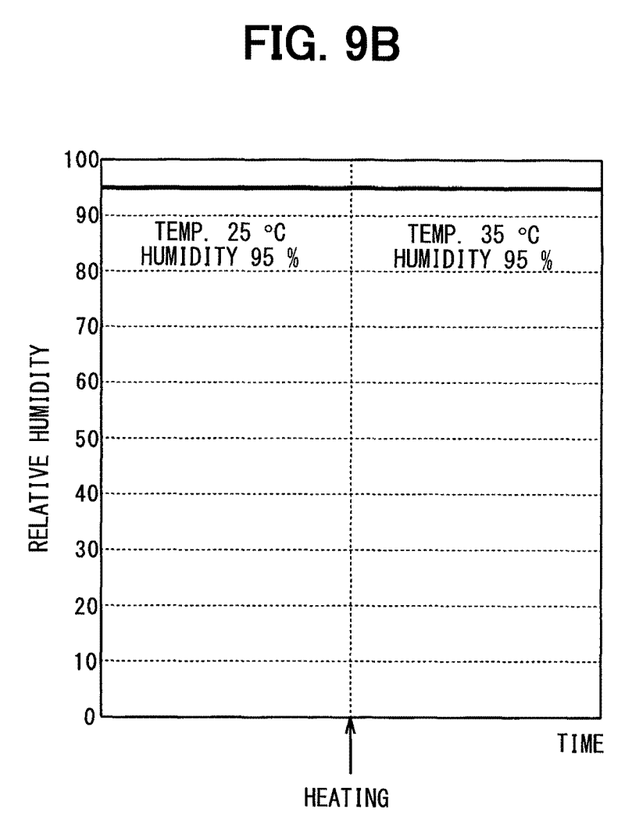
FIG. 9B is an explanatory diagram of variation of the relative humidity before or after the heating when dew condensation occurs.

Each of FIG. 9A and FIG. 9B expresses time variations of the original temperature, original relative humidity, subsequent temperature and subsequent humidity before or after the humidity-sensitive film 22 is heated.

Next, at S170, the determination device 5 determines whether a condition is satisfied in which the temperature of the intake air is equal to or higher than 30 degrees Celsius and the temperature of the operating oil of the internal combustion engine 2 is equal to or higher than 80 degrees Celsius.

When the determination device 5 determines that the condition is satisfied (i.e., YES), the processing proceeds to S180.

When the determination device 5 determines that the condition is not satisfied (i.e., NO), the processing proceeds to S230, and the heating of the humidity-sensitive film 22 by the heater 40 is suspended. Then, the processing proceeds to S240. The determination device 5 waits until the temperature of the humidity-sensitive film 22, detected by the temperature detector 39, becomes equal to the original temperature, and the determination device 5 finishes the processing.

The processing at S170 corresponds to a function of the condition determination portion 48.

Next, at S180, the determination device 5 increases the cumulated number by one, and the processing proceeds to S190.

At S190, the determination device 5 determines whether the cumulated number is more than 5.

When the determination device 5 determines that the cumulated number is more than 5 (i.e., YES), the processing proceeds to S200 to determine that the malfunction occurs. Then, the processing proceeds to S210 and the heating of the humidity-sensitive film 22 by the heater 40 is suspended. Then, the processing proceeds to S220. At S220, the determination device 5 outputs the signal to activate the alert portion 50. The processing at S150 and S200 correspond to a function of the malfunction determination portion 45.

When the determination portion 5 determines that the cumulated number is equal to or less than 5 (i.e., NO), the processing proceeds to S230 and the heating of the humidity-sensitive film 22 by the heater 40 is suspended. Then, the processing proceeds to S240. The determination device 5 waits until the temperature of the humidity-sensitive film 22, detected by the temperature detector 39, becomes equal to the original temperature, and the determination device 5 finishes the processing.

The processing at S180 and S190 correspond to a function of the cumulated number determination portion 49.

[Effects]

The determination device 5 of the present embodiment includes the malfunction determination portion 45 that determines the malfunction of the humidity detector 37 by comparing the estimated relative humidity at the subsequent temperature and the subsequent relative humidity.

That is, the determination device 5 compares the estimated relative humidity at the subsequent temperature and the actual subsequent relative humidity. For example, when a difference between the estimated relative humidity at the subsequent temperature and the actual subsequent relative humidity is quite larger than a predetermined difference, the determination device 5 determines that the malfunction occurs in the humidity detector 37.

As a result, the determination device 5 detects the malfunction of the humidity detector 37 having the humidity-sensitive film 22 located in the intake passage 6.

According to the determination device 5 of the present embodiment, the malfunction determination portion 45 executes to determine the malfunction when the control of the other device is not executed based on the relative humidity.

When the other device is controlled, the heater 40 does not heat the humidity-sensitive film 22 and the temperature of the humidity-sensitive film 22 is not increased. As a result, accuracy of the absolute humidity calculated from the psychrometric chart is secured.

The accuracy of the absolute humidity, which is evaluated from the relative humidity with the psychrometric chart, is reduced as the temperature of the humidity-sensitive film 22 is increased. The reason will be described with reference to FIG. 10.

Figure 10:
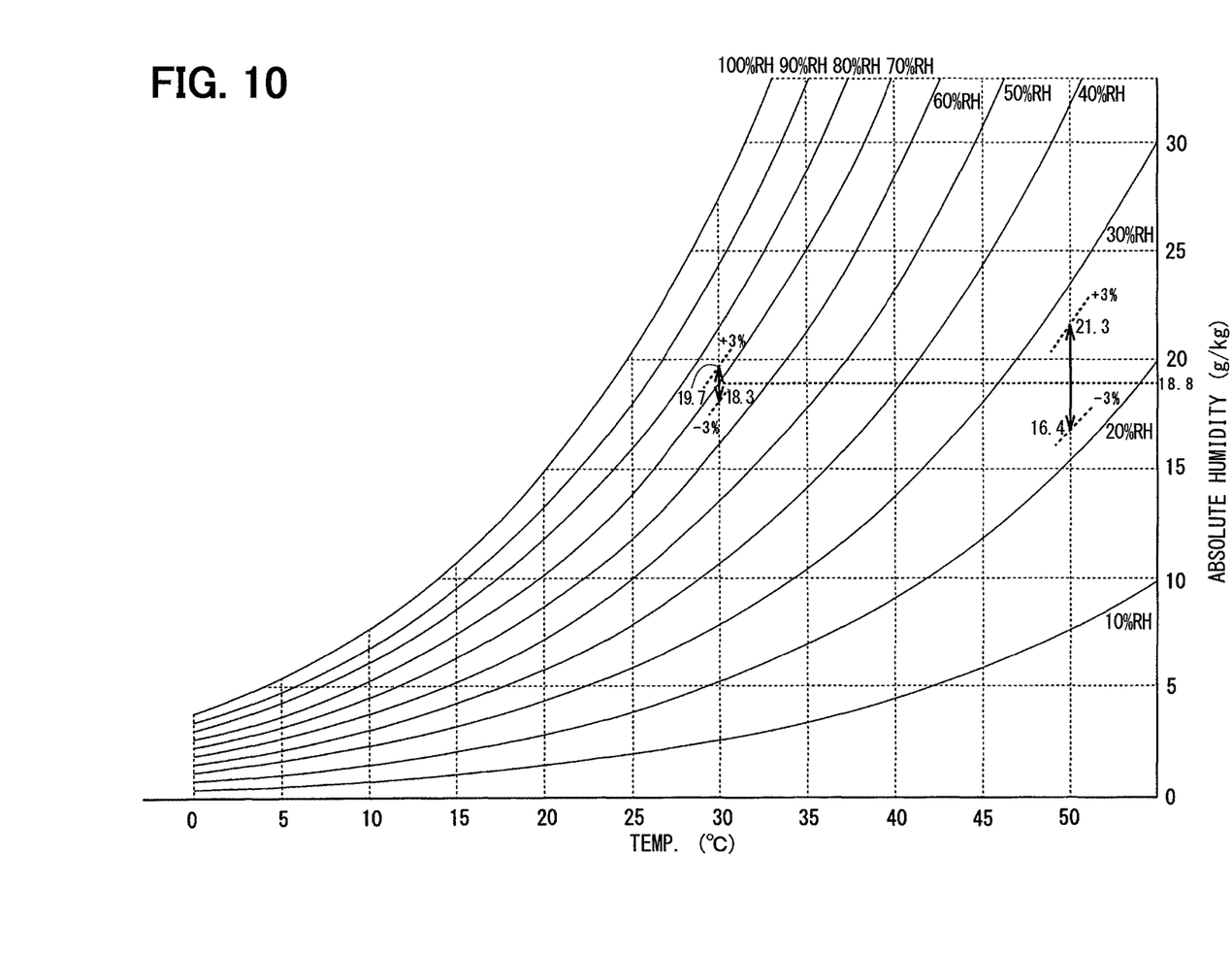
FIG. 10 is an explanatory diagram of accuracy of a temperature of the humidity-sensitive film and an absolute humidity with a psychrometric chart.

For example, the absolute humidity has variation range from 18.3 to 9.7 g/Kg, corresponding to 3 percent of vertical variation range of 70 percent relative humidity at 30 degrees Celsius of the temperature of the humidity-sensitive film 22. The absolute humidity is 18.3 g/Kg at 70 percent relative humidity and 30 degrees Celsius.

In contrast, the absolute humidity has variation range from 16.4 to 21.3 g/Kg, corresponding to 3 percent of vertical variation range at 50 degrees Celsius of the temperature of the humidity-sensitive film 22.

Namely, as the temperature of the humidity-sensitive film 22 is increased, variation range of the absolute humidity corresponding to 1 percent of variation range of the relative humidity is increased.

That is, as the temperature of the humidity-sensitive film 22 is decreased, the accuracy of the absolute humidity, which is evaluated from the psychrometric chart, is improved.

Additionally, the heater 40 heats the humidity-sensitive film 22 only when the determination device executes to determine the malfunction. Since the humidity-sensitive film 22 is not constantly heated, power consumption is also reduced.

According to the determination device 5 of the present embodiment, the control of the other device is executed based on the relative humidity after the malfunction determination portion 45 executes to determine the malfunction and the temperature of the humidity-sensitive film 22 is equal to the original temperature.

The control of the other device is executed after the temperature of the humidity-sensitive film 22 is equal to the original temperature. Therefore, the accuracy of the absolute humidity, which is calculated from the psychrometric chart, is more secured.

Alternatively, the control of the other device may be executed after the relative humidity is equal to the original relative humidity. It takes longer time for the relative humidity returning to the original relative humidity than for the temperature returning to the original temperature. Therefore, when the control of the other device is executed after the relative humidity returns to the original relative humidity, the accuracy of the absolute humidity is more secured.

According to the determination device 5 of the present embodiment, the humidity sensor 3 has the humidity sensor chip 21 including the humidity detector 37 and the heater 40 is included in the humidity sensor chip 21.

It is not necessary to dispose the heater 40 separately from the humidity sensor chip 21.

Also, the temperature detector 39 is included in the humidity sensor chip 21.

The temperature measurement portion 42 is disposed close to the humidity-sensitive film 22. As a result, the temperature of the humidity-sensitive film 22 is detected more accurately.

The temperature measurement portion 42 is disposed close to the humidity-sensitive film 22 and detection delay of the temperature increase by the heating is restricted. As a result, it is not necessary to hold the temperature of the humidity-sensitive film 22 constant during the detection of the malfunction, especially by a temperature control such as a Proportional-Integral-Differential (PID) control.

The determination device 5 of the present embodiment includes the abnormality determination portion 46, the humidity determination portion 47, the condition determination portion 48 and the cumulated number determination portion 49.

Even when the dew condensation water adheres to the humidity-sensitive film 22, the determination device 5 does not determine that the malfunction occurs.

Specifically, when the dew condensation water adheres to the humidity-sensitive film 22, the original relative humidity and the subsequent relative humidity do not change before or after the heating. The condition determination portion 48 determines whether the dew condensation water adheres to the humidity-sensitive film 22 so that the determination device 5 does not determines that the malfunction occurs when the dew condensation water adheres to the humidity-sensitive film 22. When the condition determination portion 48 determines that the dew condensation water does not adhere and the cumulated number determination portion 49 determines that the malfunction determination is repeated, the determination device 5 determines that the malfunction occurs.

According to the determination device 5, the malfunction determination portion 45 does not execute to determine the malfunction when the temperature of the intake air is equal to or lower than 10 degrees Celsius.

When the temperature of the intake air is low, the range of possible absolute humidity is narrower than when the temperature of the intake air is high. In this case, the determination device 5 executes to determine the malfunction based on the absolute humidity within such a narrow range.

In the present embodiment, the determination device 5 executes to determine the malfunction when the temperature of the intake air is higher than a predetermined temperature. As such, the absolute humidity within broader range is employed in the malfunction determination. That is, the determination device 5 executes to determine the malfunction based on the absolute humidity within the broader range. Therefore, the accuracy of the malfunction determination is improved and erroneous determination is restricted.

According to the determination device 5 of the present embodiment, the humidity sensor 3 has the terminal outputting the relative humidity, and the flow rate detector outputting the flow rate of the intake air. The flow rate is outputted through the terminal outputting the relative humidity.

As a result, the terminals of the humidity detector 37 and the flow rate detector are shared, and thus the number of the terminals is reduced.

The determination device 5 of the present embodiment outputs the signal to activate the alert portion 50 when the malfunction determination portion 45 determines that the malfunction occurs. As a result, the determination device 5 notifies a crew of the vehicle about the malfunction, and the determination device 5 restricts a situation in which the internal combustion engine 2 is continued to be operated while the malfunction occurs in the humidity detector 37.

[Modifications]

The present disclosure may include various modifications without departing from the gist of the present disclosure.

In the above embodiment, the humidity sensor chip 21 includes the heater 40. However, the heater 40 may be disposed outside of the humidity sensor chip 21.

In the above embodiment, a reference value of each of the original relative humidity and the subsequent relative humidity of the humidity determination portion 47 is equal to or higher than 90 percent. However, the reference value is not limited and may be modified.

In the above embodiment, the predetermined condition of the condition determination portion 48 is the condition where the temperature of the intake air is equal to or higher than 30 degrees Celsius and the temperature of the operating oil of the internal combustion engine 2 is equal to or higher than 80 degrees Celsius. However, the temperature of the intake air and the temperature of the operating oil of the internal combustion engine 2 are not limited in the predetermined condition and may be modified.

In the above embodiment, the cumulated number determination portion 49 determines whether the cumulated number is more than 5. However, the reference number is not limited to 5 and may be modified.

In the above embodiment, the malfunction determination portion 45 does not determine the malfunction when the temperature of the intake air is equal to or lower than 10 degrees Celsius. However, the referential temperature of the intake air is not limited to 10 degrees Celsius and may be modified.

In the above embodiment, the subsequent temperature is higher than the original temperature by the heating of the heater 40. However, the subsequent temperature may be lower than the original temperature. Specifically, the subsequent temperature is lower than the original temperature when the humidity-sensitive film 22 is initially heated by the heater 40 and then the heating by the heater 40 is suspended. Also, the subsequent temperature is lower than the original temperature when the humidity-sensitive film 22 is initially heated by the heater 40 and then the heating by the heater 40 is suppressed.

Even when the subsequent temperature is lower than the original temperature, the malfunction determination portion 45 compares the estimated relative humidity at the subsequent temperature and the actual subsequent relative humidity, and the determination portion 45 determines that the malfunction occurs in the humidity detector 37 when the difference between the estimated relative humidity and the actual subsequent humidity is quite larger than the predetermined difference.

Figure 12A:
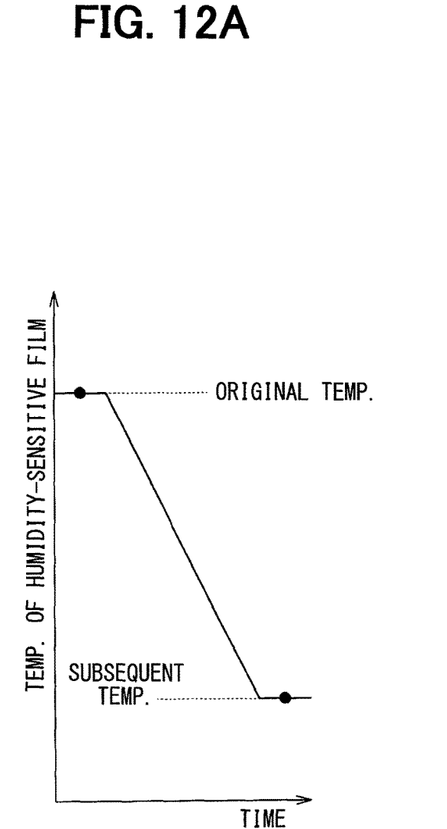
FIGS. 12A and 12B are explanatory diagrams of an original temperature and a subsequent temperature according to a modification.

As shown in FIG. 12A, the original temperature and the subsequent temperature may be temperatures in a constant temperature state before or after the temperature decrease. Alternatively, as shown in FIG. 12B, the original temperature and the subsequent temperature may be temperatures during the temperature decrease.

Figure 12B:
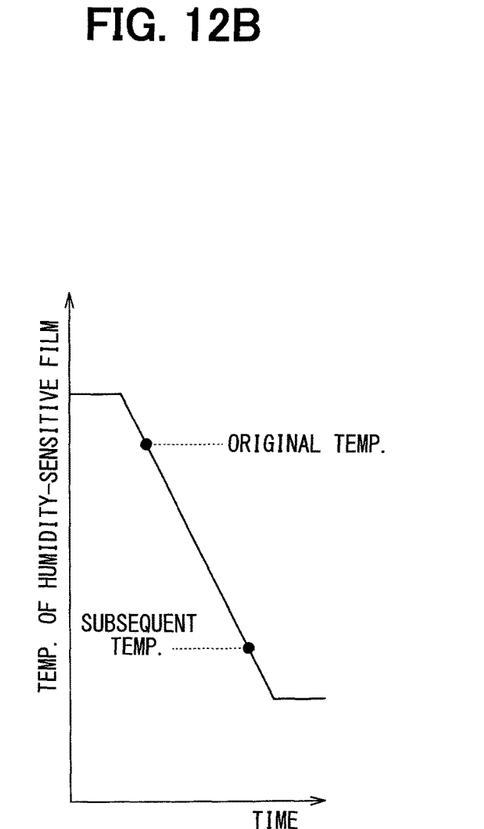

In FIG. 12A and FIG. 12B, each black spot expresses a detection time point of the original temperature or the subsequent temperature.

While only the selected exemplary embodiment and examples have been chosen to illustrate the present disclosure, it will be apparent to those skilled in the art from this disclosure that various changes and modifications can be made therein without departing from the scope of the disclosure as defined in the appended claims. Furthermore, the foregoing description of the exemplary embodiment and examples according to the present disclosure is provided for illustration only, and not for the purpose of limiting the disclosure as defined by the appended claims and their equivalents.

What is claimed is:

1. A determination device that determines malfunction of a humidity sensor,
   the humidity sensor including:
   a humidity detector that has a humidity-sensitive film and detects a relative humidity of intake air based on a capacitance of the humidity-sensitive film, the intake air being taken into an internal combustion engine for a vehicle, the humidity-sensitive film being located in an intake passage where the intake air flows;
   a temperature detector that detects a temperature of the humidity-sensitive film; and
   a heater that heats the humidity-sensitive film,
   the determination device comprising:
   a malfunction determination portion, wherein:
   the temperature of the humidity-sensitive film is increased when the humidity-sensitive film is heated by the heater;
   the temperature detected at a predetermined time point is referred to as an original temperature;
   the relative humidity at the original temperature is referred to as an original relative humidity;
   the temperature detected after the heater starts heating or after the heater stops heating is referred to as a subsequent temperature, the subsequent temperature being different from the original temperature;
   the relative humidity at the subsequent temperature is referred to as a subsequent relative humidity;
   the malfunction determination portion estimates an estimated relative humidity at the subsequent temperature from the original relative humidity and the subsequent temperature; and
   the malfunction determination portion compares the estimated relative humidity at the subsequent temperature and the subsequent relative humidity to determine malfunction of the humidity detector.

2. The determination device according to claim 1, wherein the subsequent temperature is detected after the temperature of the humidity-sensitive film is increased.

3. The determination device according to claim 1, wherein the subsequent temperature is detected after the temperature of the humidity-sensitive film is decreased.

4. The determination device according to claim 1, wherein the malfunction determination portion executes to determine the malfunction of the humidity detector when a control of a throttle valve or a fuel injection valve is not executed based on the relative humidity.

5. The determination device according to claim 4, wherein the malfunction determination portion executes to determine the malfunction of the humidity detector when energization of the humidity detector is started.

6. The determination device according to claim 4, wherein the malfunction determination portion executes to determine the malfunction of the humidity detector when a speed of the vehicle is reduced.

7. The determination device according to claim 4, wherein the malfunction determination portion executes to determine the malfunction of the humidity detector when the vehicle is stopped.

8. The determination device according to claim 1, wherein a control of a throttle valve or a fuel injection valve is executed based on the relative humidity after the malfunction determination portion executes to determine the malfunction of the humidity detector and the temperature is equal to the original temperature, or after the malfunction determination portion executes to determine the malfunction of the humidity detector and the relative humidity is equal to the original relative humidity.

9. The determination device according to claim 1, wherein
the humidity sensor has a humidity sensor chip including the humidity detector, and
the heater is included in the humidity sensor chip.

10. The determination device according to claim 9, wherein
the temperature detector is included in the humidity sensor chip.

11. The determination device according to claim 1, wherein
the humidity sensor has a humidity sensor chip including the humidity detector, and
the heater is not included in the humidity sensor chip.

12. The determination device according to claim 11, wherein
the temperature detector is included in the humidity sensor chip.

13. The determination device according to claim 1, further comprising:
an electronic control including the malfunction determination portion, the electronic control unit being configured to:
compare the estimated relative humidity at the subsequent temperature and the subsequent relative humidity to determine whether a detected relative humidity of the humidity detector is abnormal;
determine whether each of the original relative humidity and the subsequent relative humidity is equal to or higher than a predetermined relative humidity when the detected relative humidity is determined to be abnormal;
determine whether a predetermined condition is satisfied when each of the original relative humidity and the subsequent relative humidity is determined to be equal to or higher than the predetermined relative humidity;
increase a cumulated number by one when the predetermined condition is determined to be satisfied;
determine whether the cumulated number is more than a predetermined number; and
determine that the malfunction occurs in the humidity detector when the cumulated number is determined to be more than the predetermined number.

14. The determination device according to claim 13, wherein
the predetermined condition is a condition where a temperature of the intake air is equal to or higher than a first predetermined temperature and a temperature of an operating oil of the internal combustion engine is equal to or higher than a second predetermined temperature.

15. The determination device according to claim 1, wherein
the malfunction determination portion does not execute to determine the malfunction of the humidity detector when a temperature of the intake air is equal to or lower than a third predetermined temperature.

16. The determination device according to claim 1, wherein
the humidity sensor has a terminal outputting the relative humidity and a flow rate detector outputting a flow rate of the intake air, and
the flow rate is outputted through the terminal.

17. The determination device according to claim 1, wherein
the determination device outputs a signal to activate an alert portion when the malfunction determination portion determines that the malfunction occurs in the humidity detector.

\* \* \* \* \*